United States Patent [19]

Yoshida et al.

[11] Patent Number: 5,169,938
[45] Date of Patent: Dec. 8, 1992

[54] ANTI-T CELL RECEPTOR γ-CHAIN MONOCLONAL ANTIBODY

[75] Inventors: Hajime Yoshida, Sagamihara; Kenya Shitara, Machida, both of Japan

[73] Assignee: Kyowa Hakko Kogyo Co., Ltd., Tokyo, Japan

[21] Appl. No.: 184,768

[22] Filed: Apr. 22, 1988

[30] Foreign Application Priority Data

Apr. 25, 1987 [JP] Japan .................................. 62-102382
Dec. 21, 1987 [JP] Japan .................................. 62-323509

[51] Int. Cl.$^5$ .......................... C07K 3/00; C07K 13/00; C07K 15/00
[52] U.S. Cl. .......................... 530/388.22; 435/240.27; 435/7.24; 935/104; 530/388.75
[58] Field of Search ......................................... 530/387

[56] References Cited

FOREIGN PATENT DOCUMENTS

WO8800209 1/1988 PCT Int'l Appl. .
WO8902899 4/1989 PCT Int'l Appl. .

OTHER PUBLICATIONS

Brenner, et al., "Identification of a Putative Second T-Cell Receptor", Nature 322, pp. 145-149 (Jul. 10, 1986).
Nakanishi, et al., "T γ protein is expressed on murine fetal thymocytes . . . heterodimer", Nature 325, pp. 720-723 (Feb. 19, 1987).
Kranz, et al., "Limited Diversity of the Rearranged T-cell γ Gene", Nature 313, pp. 752-755 (Feb. 28, 1985).
Lew, et al., "Characterization of T Cell Receptor . . . Thymocytes", Science 234, pp. 1401-1405 (Dec. 12, 1986).
Ioannides, et al. "Identification of a second T-cell antigen receptor . . . antibody", P.N.A.S. 84, pp. 4244-4248 (Jun. 1987).
Maeda et al. "Expression of the T-cell receptor . . . Reaction", P.N.A.S. 84, pp. 6536-6540 (Sep. 1987).
*Nature*, P. Moingeon, et al., "A Gamma-chain complex forms a functional receptor on cloned human lymphocytes with natural killer-like activity", vol. 325, No. 6106, pp. 723-726, (1987).
*Nature*, P. Moingeon, et al., "A unique T-cell receptor complex expressed on human fetal lymphocytes displaying natural killer-like activity", vol. 323, No. 6087, pp. 638-640 (1986).

*Primary Examiner*—Johann Richter
*Attorney, Agent, or Firm*—Fitzpatrick, Cella, Harper & Scinto

[57] ABSTRACT

Monoclonal antibodies are disclosed capable of reacting with T cell receptor γ-chain and being useful as a reagent for investigating functions of T cell receptor γ-chain.

3 Claims, 3 Drawing Sheets

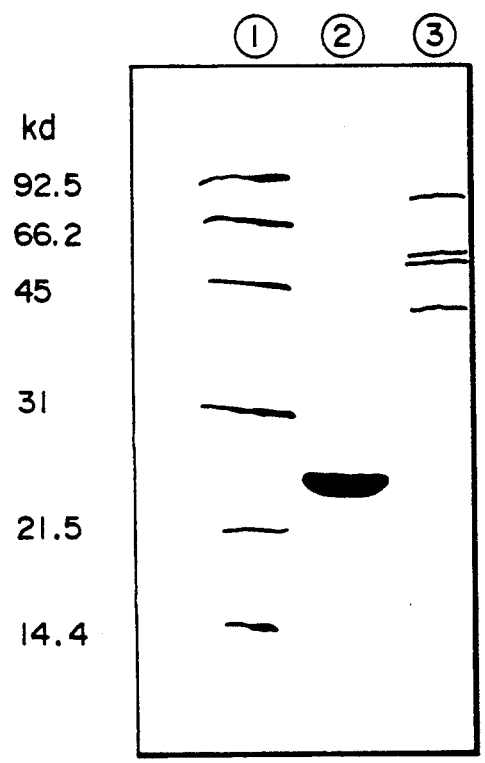 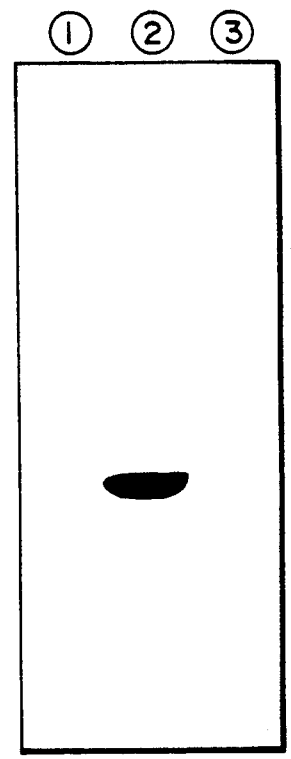

FLUORESCENCE INTENSITY

ANTI-T CELL RECEPTOR γ-CHAIN MONOCLONAL ANTIBODY

BACKGROUND OF THE INVENTION

The present invention relates to anti-T cell receptor γ-chain monoclonal antibodies which are useful as a reagent for investigating functions of T cell receptor γ-chain.

T cells play an important role in the control of immune response and in cellular immunity, of the immune system. On its surface membrane, T cell has T cell receptors, which participate in performing the functions of T cell. Studies on the structure of the receptor using a monoclonal antibody obtained from a mouse immunized with cloned T cells have revealed that it consists of two polypeptides, α- and β-chains. The sequence of the genes that encode these chains was determined by analysis based on molecular genetics. Tonegawa, et al. discovered a gene which encodes T cell receptor γ-chain (hereinafter referred to as γ-chain) as well as a gene coding for α- and β-chains, but the role played by γ-chain in the functions of T cells still remains uncertain. In addition, the presence of δ-chain linked to γ-chain was also reported [Nature, 322, 145–149 (1986)].

To elucidate the functions of γ-chain, an anlibody which specifically reacts with γ-chain is required. Mouse-derived rabbit anti-γ-chain antiserum has already been reported [Nature, 325, 720–723 (1987)], but no anti-γ-chain monoclonal antibody has not been known so far.

Moreover, in order to perform a comprehensive and more detailed investigation on γ-chain, a monoclonal antibody which has higher purity and specificity is needed.

The present inventors have found that monoclonal antibodies which react with γ-chain can be produced by hybridomas obtained by fusing spleen cells of a DBA/2 mouse immunized with the γ-chain of BALB/c mouse origin, which is expressed in *Escherichia coli* by recombinant DNA technique and murine myeloma cells, and have now completed the present invention.

SUMMARY OF THE INVENTION

The invention thus provides anti-T cell receptor γ-chain monoclonal antibodies obtained by fusing spleen cells of a mouse immunized with γ-chain and murine myeloma cell lines to generate hybridomas, selecting from among the hybridomas obtained hybridoma clones producing the monoclonal antibodies having specificity to γ-chain, and cultivating the selected hybridomas either in a suitable culture medium or administering the hybridomas to mice to thereby cause hybridoma cell propagation in the ascitic fluid, followed by separation, from the culture or the ascitic fluid, of the desired antibodies.

BRIEF DESCRIPTION OF THE DRAWINGS

In the accompanying drawings, FIG. 1 shows the assay results of the specificity of KM-367 by Western blotting in Example 2, in which FIG. 1(A) gives staining with Amide Black and FIG. 1(B) gives immunostaining with KM-367. In (A) and (B), ① shows molecular weight markers (14.4 kd: lysozyme, 21.5 kd: soybean trypsin inhibitor, 31 kd: carbonic anhydrolase, 45 kd: ovalbumin, 66.2 kd: bovine serum albumin (BSA), and 92.5 kd: phosphorylase b), ② shows γ-chain and ③ shows foreign proteins derived from host cells of a microorganism belonging to *Escherichia coli*.

DESCRIPTION OF THE INVENTION

Figure 2:
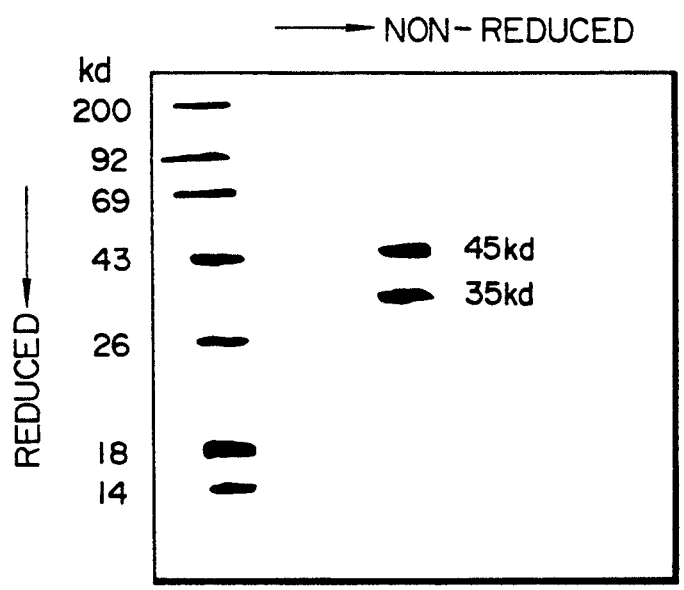
FIG. 2 shows the result of two-dimensional electrophoresis of immunoprecipitates in Example 3. The electrophoresis was performed under non-reducing conditions in the first dimension (horizontal direction) and under reducing conditions in the second dimension (vertical direction). Molecular weight markers are shown on the left lane (14 kd: lysozyme, 18 kd: β-lactoglobulin, 26 kd: α-chymotrypsinogen, 43 kd: ovalbumin, 69 kd: BSA, 92 kd: phosphorylase b, and 200 kd: myosin heavy chain).

A detail protocol for the production of monoclonal antibodies according to the present invention is as follows:

(1) Immunization of Animal and Preparation of Antibody-Producing Cells

DBA/2 mice (purchased from Shizuoka Agricultural Cooperative Association for Laboratory Animals) are immunized with γ-chain to generate antibody producing cells in spleen, lymph node and peripheral blood.

As the γ-chain, one produced in *Escherichia coli* by recombinant DNA technique based on the cDNA sequence cloned from T cells derived from BALB/c mice is used [Nature, 313, 752–755 (1985)].

The immunization is performed by administering the γ-chain (10–100 μg per animal) together with an appropriate adjuvant (e.g. Freund's complete adjuvant or aluminum hydroxide gel plus *B. pertussis* vaccine) to 8- to 10-week old DBA/2 mice subcutaneously, intravenously or intraperitoneally. Thereafter, administration of the γ-chain is repeated two to ten times at 1- to 2-week intervals.

One week after each immunization, the blood is sampled from the eyeground venous plexus and the serum of each sample is tested as to the anti-γ-chain antibody titer by the solid-phase enzyme immunoassay technique given below [Enzyme-linked Immunosorbent Assay (ELISA), published by Igaku Shoin, Tokyo 1976].

Enzyme Immunoassay Technique

The specific antigens in an amount of 100 μg per well [a suspension obtained by adding phosphate-buffered saline (PBS; 1.83 g of disodium phosphate, 0.21 g of monopotassium phosphate and 7.65 g of sodium chloride in 1 liter of distilled water; pH 7.2) so as to make the concentration of γ-chain to be 10 μg/ml; and a solution containing other type of antigen in place of γ-chain, or PBS solution containing 1% BSA (BSA/PBS) solution is used, for the study of cross reaction] are distributed into wells of a 96-well plate for EIA (product of Flow Laboratories). After allowing the plate to stand overnight at 4° C. to ensure coating of the wells with the antigens, the supernatant is removed from the plate and then the plate is washed well with deionized water or PBS. Then BSA/PBS solution is distributed into the wells (200 μl per well), and the protein-binding sites remaining on each well are blocked by allowing the plate to stand overnight at 4° C. After discarding the BSA/PBS solution, the wells are washed well with PBS. Serial dilutions of samples (mouse antisera, hybridoma culture supernatants or purified antibodies) are distributed into the wells (50 μl per well) as the first antibody, followed by overnight-standing at 4° C. or by three to four hour-standing at room temperature. After washing the wells six times with PBS, a 400-fold dilution of peroxidase-conjugated rabbit immunoglobulins to mouse immunoglobulins (product of DAKO and distributed by Kyowa Medex; used as the second antibody) is distributed into the wells (100 μl per well). The plate is then allowed to stand at room temperature for two hours.

After washing with PBS, 100 μl of an ABTS substrate solution [prepared by dissolving 550 mg of diammonium 2,2'-azinobis (3-ethylbenzothiazoline-6-sulfonate) in 1 liter of 0.1M citrate buffer (pH 4.2) and adding, just prior to use, hydrogen peroxide to a concentration of 1 μl/ml] is applied and the color developed is measured in terms of absorbance $OD_{415\,nm}$. Those mice that showing an anti-γ-chain titer higher than $10^3$ times as much as normal mice serum ($OD_{415\,nm}$) are used as sources of supply of antibody-producing cells for hybridoma production.

For submitting to cell fusion, γ-chains are intraperitoneally administered to the immunized mice in a dose of 10 to 100 μg per animal three to four days prior to the cell fusion treatment. The spleen is extirpated, cut into fragments in MEM (product of Nissui Pharmaceutical), loosened up with a pair of forceps, and centrifuged at 1200 rpm for 5 minutes. The supernatant is discarded, and the sediment is deprived of erythrocytes by treatment with Tris-ammonium chloride buffer (pH 7.65) for 1–2 minutes, washed three times with MEM and used as the spleen cells for fusion.

(2) Preparation of Myeloma Cells

A mouse-derived established myeloma cell line is preferably used. Usable examples of such cell line include the 8-azaguanine resistant murine (BALB/c-derived) myeloma cell lines P3-X63-Ag8-U1 (P3-U1) [Current Topics in Microbiology and Immunology, 81, 1-7 (1978)], P3-NS1/1-Ag4.1 (NS-1)[European J. Immunology, 6, 511-519 (1976)], SP2/0-Ag14 (SP-2) [Nature, 276, 269-270 (1978)], P3-X63-Ag8.653 (653) [J. Immunology, 123, 1548-1550 (1979)] and P3-X63-Ag8 (X63) [Nature, 256, 495-497 (1975)]. The passage of these cell lines is performed in 8-azaguanine medium [normal medium prepared by adding, to RPMI-1640 medium, glutamine (1.5 mM), 2-mercaptoethanol ($5 \times 10^{-5}$M), gentamycin (10 μg/ml) and fetal calf serum (FCS: product of CSL, 10%), with further supplementation with 8-azaguanine (15 μg/ml)]. The cell line selected for cell fusion is transferred to normal medium three to four days before fusion to ensure the cell count of not less than $2 \times 10^7$ on the day of cell fusion.

(3) Cell Fusion

The spleen cells prepared in (1) and the myeloma cells obtained in (2) are washed well with MEM or PBS, and mixed in a cell number ratio of spleen cells : myeloma cells = 5 to 10:1 and then subjected to centrifugation (1,200 rpm, 5 minutes). The supernatant is discarded and the cell sediment is loosened up. With stirring at 37° C., a mixture of 1 to 4 g of polyethylene glycol (PEG-1000–4000), 1 to 4 ml of MEM and 0.5 to 1.0 ml of dimethyl sulfoxide is added in an amount of 0.1 to 1.0 ml per $10^8$ spleen cells, and 0.5 to 3 ml of MEM is further added after 0.5 to 10 minutes. After several additions of 0.5 to 3 ml of MEM at 0.5- to 2-minute intervals, 30 to 60 ml of MEM is added. After centrifugation (900 rpm, 5 minutes), the supernatant is discarded and the cell sediment is loosened gently. To the cells is added 50 to 200 ml of the normal medium [RPMI-1640 medium with 10% FCS, glutamine (1.5 mM), 2-mercaptoethanol ($5 \times 10^{-5}$M) and gentamycin (10 μg/ml)], and the cells are gently suspended in the medium by a measuring pipette.

The suspension obtained is distributed into the wells of an incubation plate (half the volume of each well). Incubation is carried out in 3 to 7% $CO_2$ incubator at 35 to 40° C. for 10 to 30 hours. HAT medium [normal medium supplemented with hypoxanthine ($10^{-5}$ to $10^{-3}$M), thymidine ($10^{-6}$ to $10^{-4}$M) and aminopterine ($10^{-8}$ to $10^{-7}$M)] is added to the incubation plate (half the volume of each well), and incubation is conducted for a further 10 to 30 hours. Thereafter, half the volume of supernatant is discarded and the same volume of fresh HAT medium is added at 10- to 30-hour intervals for one to three days. Incubation in the $CO_2$ incubator at 35 to 40° C. is continued for 10 to 14 days.

From those wells in which fused, colony-forming grown cells are found, half the volume of supernatant is discarded and the same volume of HT medium (HAT medium minus aminopterine) is added, followed by medium replacement with fresh portions of HT medium at 10- to 30-hour intervals for one to three days.

After three to four days of cultivation in HT medium, a portion of the supernatant is collected and anti-γ-chain antibody titer is assayed by the above-mentioned enzyme immunoassay technique.

For the wells showing a certain antibody titer, cloning is repeated two to four times by the limiting dilution technique. In this way, those clones for which high antibody titer values are stably obtainable are selected as anti-γ-chain monoclonal antibody-producing hybridoma cell lines.

(4) Preparation of Monoclonal Antibodies

Eight- to ten-week-old female BALB/c nu/nu nude mice treated with pristane [intraperitoneally administered with 0.5 ml of 2,6,10,14-tetramethylpentadecane (pristane) and fed for one to two weeks] are intraperitoneally injected with the anti-γ-chain monoclonal antibody-producing hybridoma obtained in procedure (3) at a dose of $2-4 \times 10^6$ cells per animal. Within 10–21 days, the hybridoma cells produce ascites carcinoma in the mice. The ascitic fluid is collected from such mice, centrifuged (3000 rpm, 5 minutes) to remove solids, subjected to salting out with 50% and 40% ammonium sulfate, and dialyzed against PBS (pH 7.2) for one to two days. The dialyzate is collected as a partially purified monoclonal antibody, which may be used for quantitative analysis.

When further purification is needed, the partially purified monoclonal antibody is passed through a DEAE-Sepharose column or protein-A-Sepharose column, and the IgG fraction is collected.

The isotype and subclass of the antibody is determined by the Ouchterlony's method (double immunodiffusion) as described in [Seibutsukagaku Jikkenho (Methods of Experimental Biochemistry) vol. 15, Introduction to Experimental Immunology, p.74, Gakkai Shuppan Center, 1981].

The quantity of protein is estimated by the Folin's method, followed by calculation based on the absorbance at 280 nm [1.4 ($OD_{280}$) approximately corresponds to 1 mg of immunoglobulin per ml].

It was determined that monoclonal antibodies KM-367, KM-365 and KM-369 obtained from hybridoma cell lines named KM-367, KM-365 and KM-369 belong to $IgG_1$, $IgG_{2b}$ and $IgG_1$ respectively.

The monoclonal antibodies KM-367, KM-365 and KM-369 have specificity to γ-chain. Therefore, the monoclonal antibodies KM-367, KM-365 and KM-369 are useful as a reagent for investigating functions of T cell receptor γ-chain. The monoclonal antibodies KM-365 and KM-369 have reactivity with γ-chain in cell-disrupted suspension of thymocyte which expresses γ-and δ-chains thereon, and the monoclonal antibody KM-369 has reactivity with γ-chain of ethanol-fixed murine T cell hybridoma cell line which expresses γ- and δ-chains thereon.

The Western blotting technique used in the Examples is a modified one of the method of Towbine et al. [Proc. Natl. Acad. Sci., 76, 4354 (1979)]. Proteins are subjected to SDS-polyacrylamide gel electrophoresis, and the gel is placed on a sheet of nitrocellulose. Blotting is carried out at 40V, 600mA at 10° C. or lower in a buffer solution [containing 3 g/l Tris(hydroxymethyl)aminomethane, 14.4 g/l glycine and 20% methanol; pH 8.3] using an electrophoretic transfer blotting apparatus (product of ATTO), thereby transferring the proteins to the nitrocellulose sheet. The nitrocellulose sheet is air-dried, blocked with 3% gelatin solution, washed with water, and soaked in anti-γ-chain hybridoma supernatant at room temperature for two hours to complete the reaction. The sheet is then soaked in a solution of peroxidase-conjugated rabbit immunoglobulins to mouse immunoglobulins (product of DAKO and distributed by Kyowa Medex) at room temperature for two hours and washed with PBS containing 0.05% Tween 20 (product of Wako Pure Chemicals). It is finally soaked in a color developer to develop color and the reaction is terminated with cold water. The color developer is prepared by mixing at room temperature, (A)a solution of 100 ml of Tris-HCl buffered saline (TBS) [2.42 g Tris(hydroxymethyl)aminomethane and 29.24 g of sodium chloride in 1 liter of distilled water; pH 7.5] and 60 μl of 30% hydrogen peroxide; with (B)a solution obtained by adding 20 ml of ice-cold methanol to 60 mg of HRP color development reagent (product of BIO-RAD) in the dark at room temperature.

The electrophoresis for immune precipitate is carried out according to the method of Nakanishi, et al. [Nature, 325, 720 (1987)]. Thymocytes of fetal BALB/c mouse or C57BL/6 mouse on the 17th day of fetal life are labeled with $^{125}I$ by the lactoperoxidase method [Methods of Immunology, 178 (1977)]. In case of immunoprecipitation under non-reducing condition, the cell are washed three times with PBS, suspended in ice-cold NP40 buffer [10 mM Tris-HCl buffer (pH 7.5) with lmM phenylmethylsulfonyl fluoride and 10% Nonidet 40 (product of Particle Data Laboratories) added thereto], and disrupted by vigorous shaking. Each of the monoclonal antibodies KM-367, KM-365 and KM-369 is added to the resulting disrupted suspension to effect immune precipitation. In case of immunoprecipitation under reducing condition, the cells are washed with PBS, suspended in ice-cold NP40 buffer supplemented with 2 mM dithiothreitol and disrupted by vigorous shaking. Each of the monoclonal antibody KM-367, KM-365 and KM-369 is added to the resulting disrupted suspension to effect immune precipitation. When the one-dimentional electrophoresis is carried out, the immunoprecipitates under reducing condition is subjected to electrophoresis using 12% polyacrylamide gel according to the method of Laemmli [Nature, 227, 680(1970)]. When the two-dimmentional electrophoresis is carried out, the immunoprecipitates under non-reducing condition is subjected to electrophoresis in the first dimension using 10% polyacrylamide gel prepared inside a glass tube 1.5 mm in internal diameter. After the electrophoresis, the gel is taken out from the glass tube, held in a buffer solution containing 5% 2-mercaptoethanol at room temperature for 30 minutes, and then placed on a 12% slab gel to be subjected to electrophoresis in the second dimension.

Immunofluorescence staining of cells treated with ethanol is carried out according to the method of Brenner, et al. [Nature, 322, 145 (1986)]. Murine T cell hybridoma cell line KN6, which expresses γ- and δ-chains on the membrane surface, murine T cell hybridoma cell line KN3, which expresses α- and β-chains but not γ- and δ-chains on the membrane surface and murine T cell leukemia cell line BW5147 [J. Immunol. 110, 1470 (1973)], which is host cell line of KN6 and KN3, not expressed any of α-, β-, γ- and δ-chains, and used as the control, are suspended in PBS (pH7.2), respectively and distributed, in 180 μl-portions, into an Eppendorf tube in amount of $10^7$ cells. 140 μl of 95% ethanol-PBS solution is added to the tube at −20° C. to ensure ethanol final concentration of 70%, and incubation is carried out for 10 minutes at 4° C. The cells are washed three times with PBS and each of a culture supernatant of the monoclonal antibodies KM-367, KM-365 and KM-369 is added thereto. Incubation is carried out at 4° C. for 30 minutes. Then, the cells are washed three times with PBS supplemented with 0.1% BSA and 0.1% sodium azide and 30 μl of a 15-fold dilution of biotin-labeled goat anti-mouse immunoglobulin antiserum (product of Kirkgaard Terry) is added thereto, and incubation is carried out at 4° C. for 30 minutes. After washing three times with PBS supplemented with 0.1% BSA and 0.1% sodium azide, 20 μl of Phycoerythrine-streptavidin (product of Beckton-Dickinson) is added to the cells, and incubation is carried out at 4° C. for 30 minutes. After washing three times with PBS supplemented with 0.1% BSA and 0.1% sodium azide, the cells are suspended in 200 μl of PBS supplemented with 0.1% sodium azide. Immunofluorescence intensity is detected by the cell sorter (FCS-1, product of Japan Spectroscopic Co., Ltd.) to measure the count of antibodies.

Murine T cell hybridomas KN3 and KN6 have been deposited under the Budapest Treaty with Fermentation Research Institute, Agency of Industrial Science and Technology, Japan, on Apr. 14, 1988 as FERM BP-1854 and FERM BP-1853, respectively.

Certain specific embodiments of the present invention are illustrated by the following examples.

EXAMPLE 1

(1) Preparation of Antibody-Producing Cells

Five 8-week-old female DBA/2 mice (purchased from Shizuoka Agricultural Cooperative Association for Laboratory Animals) were intraperitoneally administered with γ-chain as antigen (100 μg per animal) together with aluminum hydroxide gel (2 mg per animal) and killed B. pertussis vaccine ($1 \times 10^9$ cells per animal; product of Chiba Serum Research Institute) as adjuvant.

Thereafter, immunization was repeated with said γ-chain without adjuvant at a dose of 100 μg per animal at 2-week intervals. From the third immunization on, the blood was sampled from the eyeground venous plexus five to seven days after each immunization, and the serum of each sample was tested as to the anti-γ-chain antibody titer by the above-mentioned solid-phase enzyme immunoassay.

Antibody titer was observed with all the test animals from the third immunization on, but immunization was repeated five times to ensure efficient production of anti-γ-chain monoclonal antibodies.

After the fifth immunization, the γ-chain was again intraperitoneally administered at a dose of 100 μg per animal, and the spleen cells were prepared from such mice three days later and submitted to cell fusion.

(2) Preparation of Myeloma Cells

The 8-azaguanine-resistant mouse myeloma cell line P3-U1 was cultivated in a normal medium (RPMI-1640 medium supplemented with 1.5 mM glutamine, $5 \times 10^{-5}$M 2-mercaptoethanol, 10 μg/ml gentamycin and 10% FCS) to thereby secure not less than $2 \times 10^7$ cells after four days.

(3) Hybridoma Production

The spleen cells ($1 \times 10^8$ cells) and murine myeloma cells ($2 \times 10^7$ cells) obtained in (1) and (2) respectively were washed well with MEM and mixed and then the mixture was subjected to centrifugation (1,200 rpm, 5 minutes).

The supernatant is discarded and the cell sediment was loosened up. With stirring at 37° C., a mixture of 2 g polyethylene glycol-1000 (PEG-1000), 2 ml of MEM and 0.7 ml of dimethyl sulfoxide was added in amount of 0.5 ml per $10^8$ spleen cells, and 1 ml of MEM was further added one minute later. After 5-additions of 1 ml of MEM at 1-minute intervals, MEM was added until the whole volume was made 50 ml. After centrifugation at 900 rpm for 5 minutes, the supernatant was discarded and the cell sediment was loosened gently. To the cell was added 100 ml of normal medium. The cells were gently suspended in the medium by a 10 ml-measuring pipette.

The suspension obtained was distributed in 1 ml-portions into the wells of a 24-well incubation plate (product of Flow Laboratories). Incubation was carried out in a 5% $CO_2$ incubator at 37° C. for 24 hours. HAT medium [the above-mentioned normal medium supplemented with hypoxanthine ($10^{-4}$M), thymidine ($1.5 \times 10^5$M) and aminopterine ($4 \times 10^{-7}$M)] was added to the incubation plate (1 ml per well) and incubation was conducted for a further 24 hours. Thereafter, 1 ml of the culture supernatant was discarded and the same volume of fresh HAT medium was added, and incubation in the $CO_2$ incubator at 37° C. was continued for 24 hours. Thereafter, 1 ml of culture supernatant was discarded and the same volume of fresh HAT medium was added. Incubation was further continued at 37° C. for 10 to 14 days.

From those wells in which fused, colony-forming grown cells were found, 1 ml of the supernatant was discarded and the same volume of HT medium was added. Incubation was continued at 37° C. The medium replacement with fresh HT medium was repeated in the same way for two days, followed by incubation for four days. A portion of culture supernatant was collected and assayed for anti-γ-chain antibody titer by the above-mentioned solid-phase enzyme immunoassay technique.

For the wells showing a certain antibody titer, cloning was repeated twice by the limiting dilution technique. In this way, three clones for which high antibody titer values were stably obtainable, KM-367, KM-365 and KM-369 were selected as anti-γ-chain monoclonal antibody-producing hybridoma cell lines. Hybridoma cell lines KM-367, KM-365 and KM-369 have been deposited under the Budapest Treaty with European Collection of Animal Cell Cultures, Great Britain, on Apr. 16, May 21, and Aug. 6, 1987 as ECACC Deposit No. 87041604, No. 87052101 and No. 87080601, respectively.

(4) Partial Purification of Antibodies

Pristane-treated 8-week old female BALB/c nu/nu nude mice were intraperitoneally injected with each of the hybridoma cell lines obtained in (3) at a dose of $4 \times 10^6$ cells per animal. In 10–21 days, the hybridoma cells produced ascites carcinoma. The ascitic fluid was collected from such mice (4–10 ml per animal), deprived of solids by centrifugation (3000 rpm, 5 minutes), subjected to salting out with 50% and with 40% ammonium sulfate, and dialyzed against PBS (pH 7.2) for two days, giving partially purified monoclonal antibodies KM-367, KM-365 and KM-369.

(5) Antigen-Specificity of Partially Purified Monoclonal Antibodies

Antigen-specificity of the thus-obtained partially purified monoclonal antibodies was examined by the solid-phase enzyme immunoassay using, as antigen, γ-chain produced in *Escherichia coli*, other proteins derived from host cells of *Escherichia coli* and bovine serum albumin (BSA) (product of Seikagaku Kogyo Co., Ltd.).

The result is summarized in Table 1.

TABLE 1

| | | Binding activity ($OD_{415nm}$) | | |
|---|---|---|---|---|
| Antibody | Concentration or dilution | γ-chain | BSA | Other proteins derived from host cells |
| Normal mouse serum | $\times 10^{-2}$ | 0.001 | 0.000 | 0.130 |
| γ-chain-immunized mouse serum | $\times 10^{-2}$ | 1.750 | 0.005 | 0.340 |
| Partially purified KM-367 | 10 μg/ml | 1.550 | 0.005 | 0.025 |
| Partially purified KM-365 | 10 μg/ml | 1.780 | 0.005 | 0.001 |
| Partially purified KM-369 | 10 μg/ml | 1.993 | 0.000 | 0.000 | volume 1 ml). A non-adsorbed IgG fraction was collected and used as highly-purified antibody.

(6) Classification of Monoclonal Antibodies

Isotype and subclass of monoclonal antibodies KM-367, KM-365 and KM-369 was determined by Ouchterlony's method to be $IgG_1$, $IgG_{2b}$ and $IgG_1$, respectively.

EXAMPLE 2

Reactivity of KM-367 with γ-chain produced in *Escherichia coli* was examined by the Western blotting technique described above. The result is shown in FIG. 1. It was demonstrated that KM-367 specifically reacts with γ-chain.

A similar result was obtained also with KM-365 and KM-369.

EXAMPLE 3

Reactivity of KM-365 with thymocytes having γ-chain expressed thereon from fetal C57BL/6 mice on the 17th day of fetal life was examined by the one-dimensional electrophoresis and two-dimensional electrophoresis for immunoprecipitates. The result of the two-dimensional electrophoresis is shown in FIG. 2. It was demonstrated that precipitates by KM-365 contained γ-chain (35 kd) and δ-chain (45 kd). The one-dimensional electrophoresis shows KM-365 immunoprecipitates γ-chain but not δ-chain under reducing condition. These results shows that KM-365 has reactivity with γ-chain but not δ-chain and that δ-chain is linked to γ-chain through the disulfide bond.

A similar result was obtained also with fetal thymocytes from a BALB/c mouse.

A similar result was obtained with KM-369, but not with KM-367.

EXAMPLE 4

According to the above-mentioned immunofluorescence staining procedure, the reactivities of KM-369 to murine T cell hybridoma cell line KN6, which expressed γ- and δ-chains on the cell surface, murine T cell hybridoma cell line KN3 which expressed α- and β-chains but not γ- and δ-chains on the cell surface, and murine T cell leukemia BW5147 which was host cell line, not expressed any of α-, β-, γ- and δ-chains, and used as control, were examined after the cell lines were fixed with treatment of ethanol.

Figure 3A:
FIG. 3 shows the result of immunofluorescence staining in Example 4, in which FIG. 3(a) gives the reactivity of KM-369 with BW5147, FIG. 3(b) gives the reactivity of KM-369 with KN3 and FIG. 3(c) gives the reactivity of KM-369 with KN6.
Figure 3B:
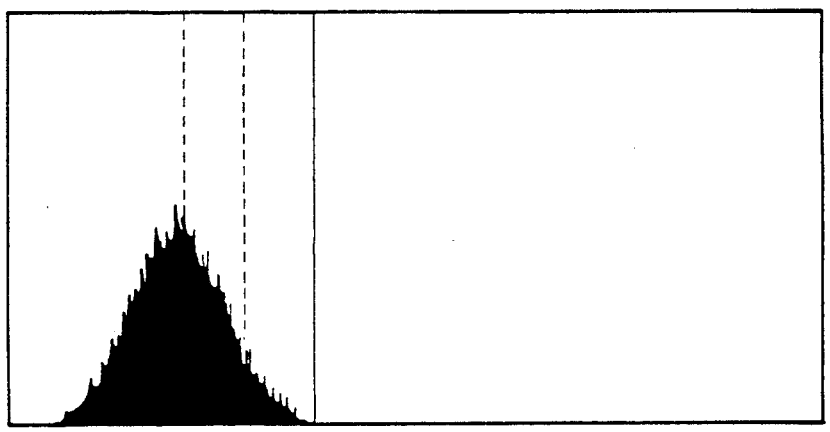
Figure 3C:
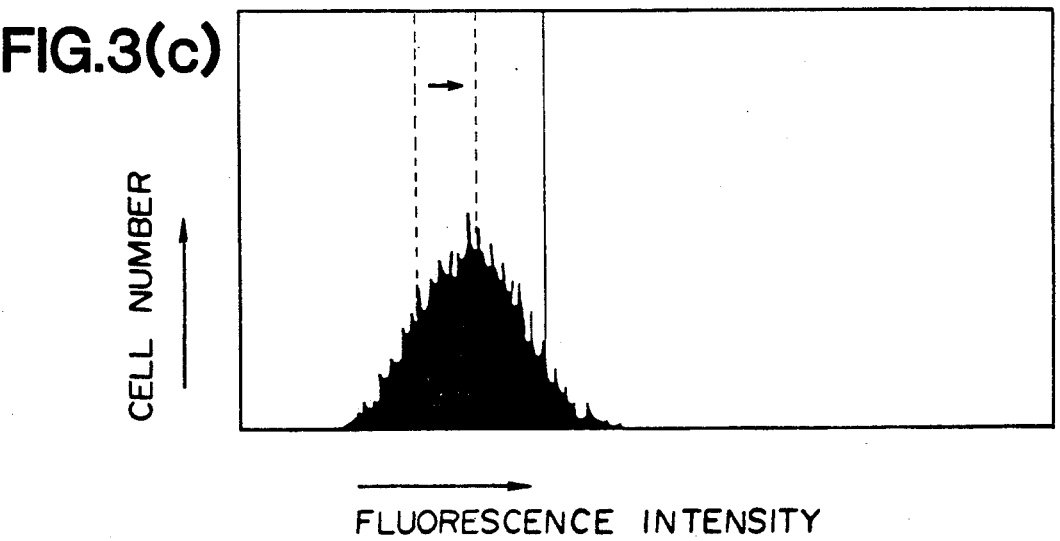

The results are shown in FIG. 3. The relative fluorescence intensity to KN3 coincide with that to BW5147. The peak position of the relative fluorescence intensity to KN6 was moved to the right direction (high area) compared with that to BW5147. It is shown that the monoclonal antibody KM-369 reacted with KN6.

As the results, it was proved that the monoclonal antibody KM-369 which was shown to be capable of reacting with γ-chain in the cell-disrupted suspension in Example 3, was capable of reacting with γ-chain on the ethanol-fixed cell membrane.

Using KM-367 and KM-365 in place of KM-369, the immunofluorescence staining procedure was repeated, but no reactivity to any of KN6, KN3 and BW5147 was observed.

What is claimed is:

1. A monoclonal antibody which is specific to T cell receptor gamma-chain of T cell receptor, obtained from hybridoma cell line KM-367 (ECACC Deposit No. 87041604).

2. A monoclonal antibody which is specific to T cell receptor gamma-chain of T cell receptor, obtained from hybridoma cell line KM-369 (ECACC Deposit No. 87080601).

3. A monoclonal antibody which is specific to T cell receptor gamma-chain of T cell receptor, obtained from hybridoma cell line KM-365 (ECACC Deposit No. 87052101).

* * * * *